United States Patent [19]

Sheridan

[11] 4,109,659
[45] Aug. 29, 1978

[54] EVAGINATION CATHETERS

[75] Inventor: David S. Sheridan, Argyle, N.Y.

[73] Assignee: Mallinckrodt, Inc., St. Louis, Mo.

[21] Appl. No.: 706,819

[22] Filed: Jul. 19, 1976

[51] Int. Cl.² ............................................. A61M 25/00
[52] U.S. Cl. .................................. 128/349 R; 128/262
[58] Field of Search ......................... 128/262, 348–351

[56] References Cited

U.S. PATENT DOCUMENTS

| 3,502,069 | 3/1970 | Silverman .................. 128/262 X |
| 3,982,544 | 9/1976 | Dyck ........................... 128/349 B X |
| 4,043,345 | 8/1977 | Kramann et al. ............. 128/349 R |

FOREIGN PATENT DOCUMENTS

| 454,642 | 3/1926 | Fed. Rep. of Germany ........... 128/262 |
| 2,421,294 | 12/1975 | Fed. Rep. of Germany ...... 128/349 R |

*Primary Examiner*—Dalton L. Truluck
*Attorney, Agent, or Firm*—Carroll F. Palmer

[57] ABSTRACT

Urinary evagination catheters comprising a rigid tube and a flexible invaginated hose are provided with a novel stopper arrangement in the ported distal end of the hose that remains closed until the hose is fully everted from the tube at which point it automatically opens to permit fluid flow through the catheter. This eliminates the need for a push rod or the like to evert the hose and permits it to be everted simply by fluid pressure applied to the proximal end of the catheter. Methods for producing the new catheters are described.

1 Claim, 13 Drawing Figures

U.S. Patent  Aug. 29, 1978  Sheet 1 of 2  4,109,659
FIG.1
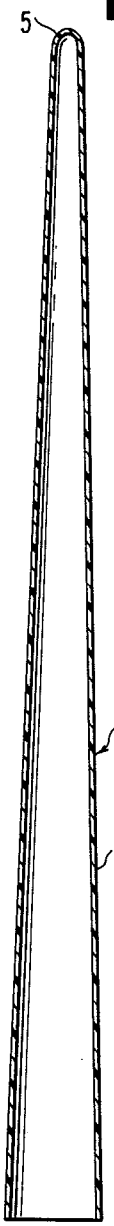
FIG.2a FIG.2b FIG.2c
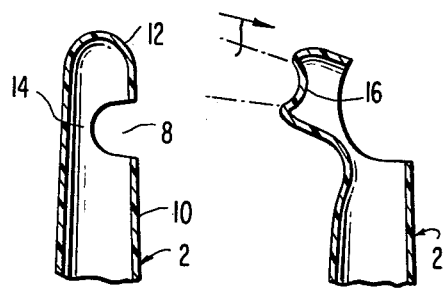
FIG.2d FIG.2e FIG.2f
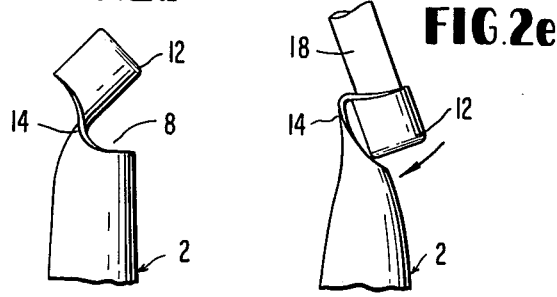
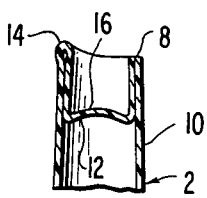
FIG.3
FIG.4
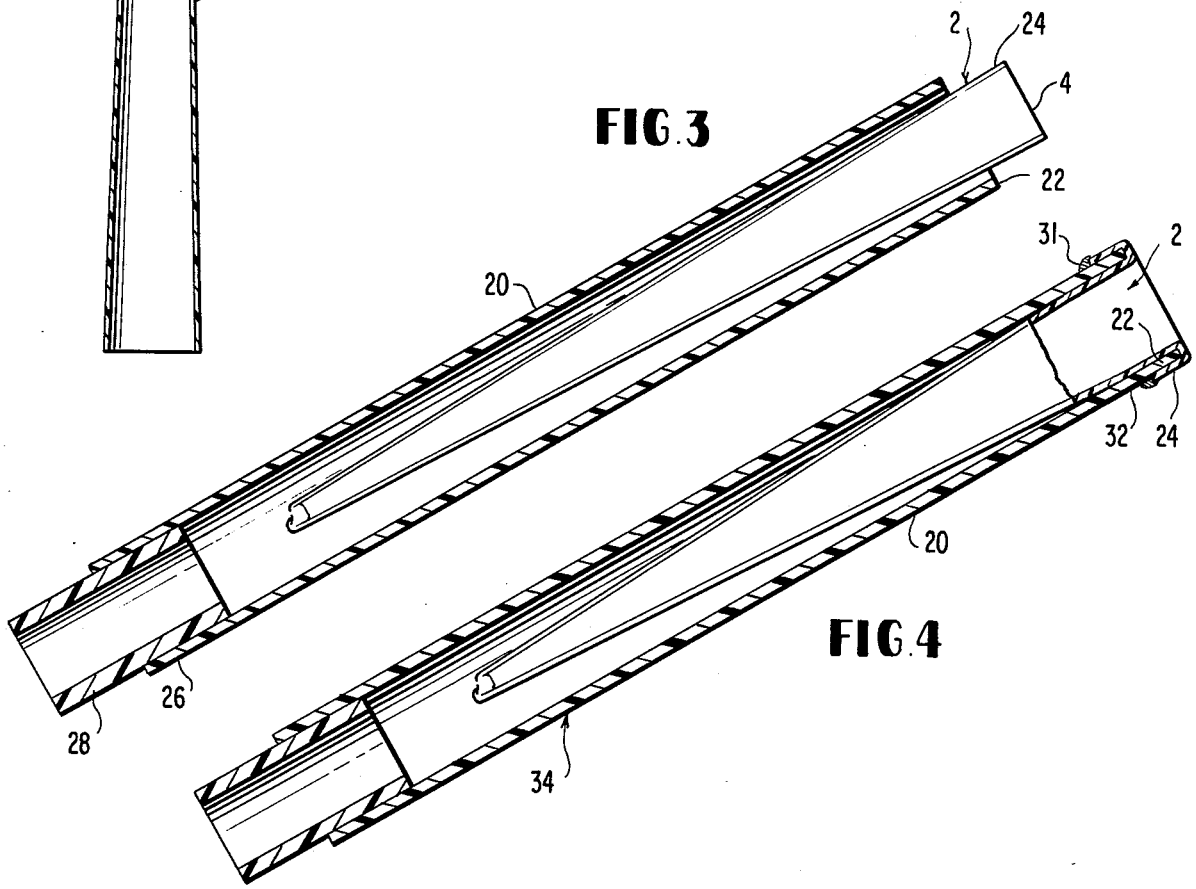

EVAGINATION CATHETERS

BACKGROUND OF THE INVENTION

1. Field of the Invention

This invention relates to evagination catheters which are used to obtain urine from the bladder for examination or drainage or to medicate the bladder. More particularly, it concerns evagination catheters that may be everted through the urethra into the bladder without vesical contamination. The invention also concerns methods for producing the new catheters.

2. Description of the Prior Art

Two methods are in general use for obtaining a sterile urine specimen or emptying the bladder, i.e., (a) catheterization and (b) suprapubic needle aspiration. Catheterization involves risk of vesical contamination, since relative movement of the outside of a standard push-in type catheter and the urethral mucosa can result in urethral flora being shoved into the bladder. If a catheter is introduced into the bladder without such movement, post-catheterization bacteriuria can be mitigated. Eversion of a catheter through the urethra avoids such relative movement, but problems of accomplishing such eversion in a clinically effective manner have impeded the utilization of this technique.

Although suprapubic aspiration avoids contamination problems, it is a much more difficult procedure and is avoided when possible.

The problem of maintaining sterility during intubation of the female urethra is discussed in U.S. Pat. No. 3,583,391. That patent discloses a catheter device in which a cot portion may be everted in such a way that movement does not take place between the outer surface of the cot and the urethal mucosa. The device is an outgrowth of an earlier everting cot of Helmholz, J. Urol., 64: 158 (1950). Other devices utilizing the principle of an everting cot or tube are disclosed in U.S. Pat. Nos. 3,332,424; 3,506,011; 3,589,356 and 3,669,099.

The evagination catheter of Cox et al (U.S. Pat. No. 3,583,391) requires a push catheter to accomplish the evertion of the cot through the urethra. The elimination of this push catheter is desirable. Thus, it presents a possible source of injury during evagination and difficulties are encountered in connecting the tip of the push catheter to the distal end of the everting cot.

OBJECTS

A principle object of this invention is the provision of improvements in evagination catheters. Further objects include the provision of:

(1) new forms of urinary evagination catheters having a novel stopper arrangement that will automatically open at the completion of evagination to permit fluid flow through the catheter.

(2) such catheters which are of uncomplicated construction and reliable in operation.

(3) new methods for producing urinary evagination catheters.

(4) urinary evagination catheters that do not require a push rod or equivalent means to perform evagination.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are in part accomplished according to the present invention by the production of evagination catheters comprising the steps of providing a substantially rigid tube open at both ends and a flexible hose shorter in length and smaller in diameter than said tube, said hose having a closed end, and an open end, the hose preferably tapering from the open end down to a smaller closed end. Advantageously, the hose has a varying wall thickness, being thicker at the large end of the taper and gradually thinning toward the small end. A port is cut in the side of the hose adjacent the closed end and leaving the tip as a pendant upon the now ported end of the hose. This tip is next inverted and inserted into the hose through the port forming a removable stopper for the hose port. The hose is then inserted small end first into the tube to such an extent that a short section of the open end of the hose remains outside of one end of the tube. This short section is folded back over the outside of the tube and a fluid-tight connection is made between the short section of hose and the adjoining outside of the tube, advantageously by applying sealing material to the junction between the end of the hose and the outside of the tube.

The objects are also in part accomplished by the provision of the new evagination catheters made in the foregoing manner.

BRIEF DESCRIPTION OF THE DRAWINGS

A more complete understanding of the new catheters and their methods of production can be had by reference to the accompanying drawings in which:

FIG. 1 is a sectional view of a flexible hose for use in forming a vagination catheter of the invention.

FIGS. 2a–2f illustrate steps in forming a stoppered distal end on hose of FIG. 1.

FIG. 3 is a sectional view of the stoppered hose inserted into the rigid tube portion of the catheter.

FIG. 4 is a sectional view showing how the open end of the hose is fixed to the tube.

DESCRIPTION OF THE PREFERRED EMBODIMENTS

Figure 5:
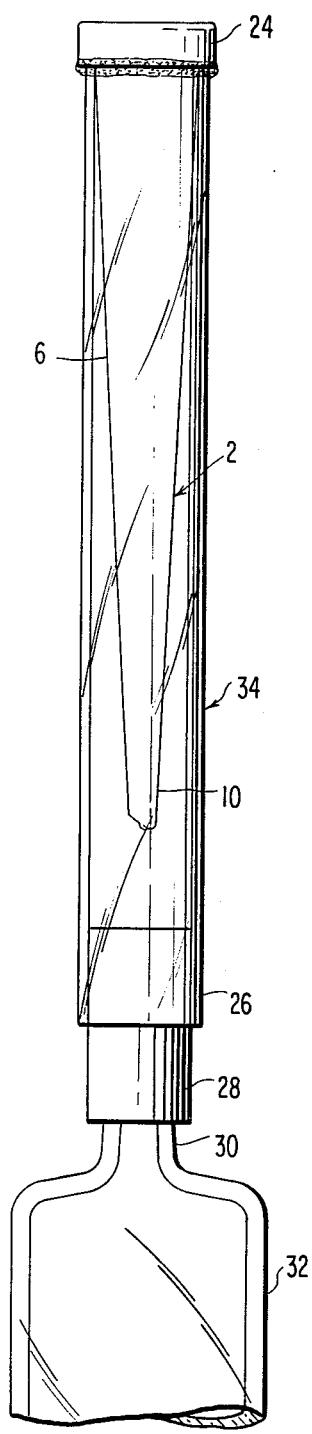
FIG. 5 is a fragmentary plan view of the catheter of FIG. 4 fitted to a syringe ready for exsertion of the flexible hose.

Referring in detail to the drawings, the flexible hose 2 has an open end 4 and a closed end 5 with the central tubular section 6 tapering from the larger end 4 to the smaller end 6. The hose 2 is formed of flexible plastic or rubber, e.g., by casting polyvinyl chloride plastisol or liquid rubber on a suitable mendrel.

With reference to FIGS. 2a–2f, a port 8 is cut in the side wall 10 of the hose 2 leaving the tip 12 pending upon the hose 2 by the uncut wall portion 14. By pushing with a small instrument upon the center 16 of the hose tip 12 (see FIG. 2b), the tip can be inverted, or turned inside out, as shown in section in FIG. 2c and in plan view in FIG. 2d. A small rod 18 is next inserted in the inverted tip 12 (see FIG. 2e) and it is shoved into the port 8 which now forms an open end upon the hose 2. Upon withdrawal of the rod 18, the inverted tip 12 forms a removal stopper for the port 8 of the hose 2 as shown in section in FIG. 2f.

The hose 2 is inserted into a substantially rigid tube 20 through the open end 22 leaving a short section 24 of the open end 4 of the hose 2 external of the tube 20. The other open end 26 is preferrably provided with an adapter 28 to permit the catheter to be fitted to the Luer end 30 of a syringe 32 (see FIG. 5).

The tube 20 may be formed of plastic or rubber, e.g., by extrusion or molding of plasticized polyvinyl chloride resin. The adapter 28 may be similarly formed of the same or different material. The adapter 28 is advantageously cemented into the tube end 26. Alternatively, the tube 20 and adapter 28 may be formed integrally, e.g., by injection molding.

The exposed end 24 of hose 2 is slightly stretched and folded back over the open end 22 of tube 2 and a thin layer 30 of sealing material is applied to the junction of the hose end 24 with the outside wall 32 of the tube 20. Any other means, e.g., a shrink-tight connection of the hose end 24 upon the tube end 22. This completes the production of the evagination catheter 34.

In accordance with demands and practices of the medical profession, the new catheters can be made in a variety of sizes varying both as to diameter and length. Advantageously, they are formed of transparent plastic, but they may also be made translucent or opaque. Preferrably, each catheter will be separately packaged and then sterilized, e.g., by exposure to ethylene oxide vapors, so that the catheter will be in sterile condition when removed from the package for evagination in a patient.

Evagination of the catheter 34 is accomplished by first mounting the adaptor 28 to the Luer tip of a syringe 32. The syringe 32 is preferrably filled with isotonic saline solution. It may also be filled with sterile air or other appropriate gas. With this assembly, the overlapped end 24 is positioned against the urethral meatus (not shown) of the patient. Then by manipulation of the syringe 32, fluid pressure is applied to the catheter interior through the proximal end 36. This causes the hose 2 to collapse. Such action tends to tighten the hose 2 about the stopper 12 ensuring its sealing of the distal end of the hose until completion of the evagination.

Figure 6:
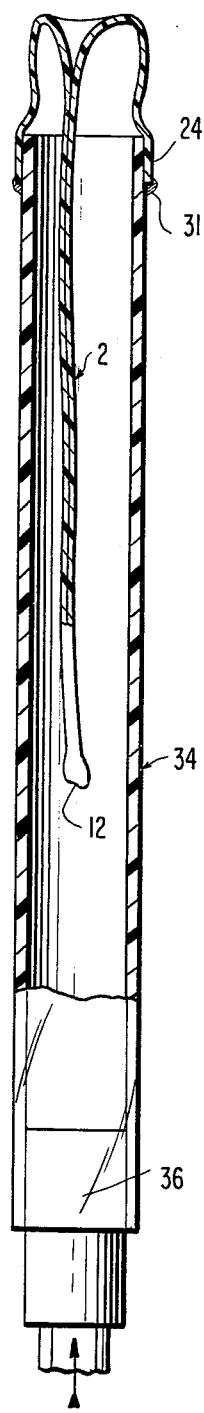
FIG. 6 is a fragmentary sectional view showing an initial stage in exsertion of the flexible hose.

Application of further pressure from the syringe 32 causes the hose 2 to begin to evert as shown in FIG. 6. The hose end 24 remains stationary relative to the urethral meatus and as the hose 2 everts, further new sterile portions of the formerly inside wall of the hose are laid down upon the urethral mucosa, i.e., there is no relative movement between the urethral mucosa and the facing wall of the hose 2. Hence, evagination does not serve to shove urethral flora into the bladder.

Figure 7:
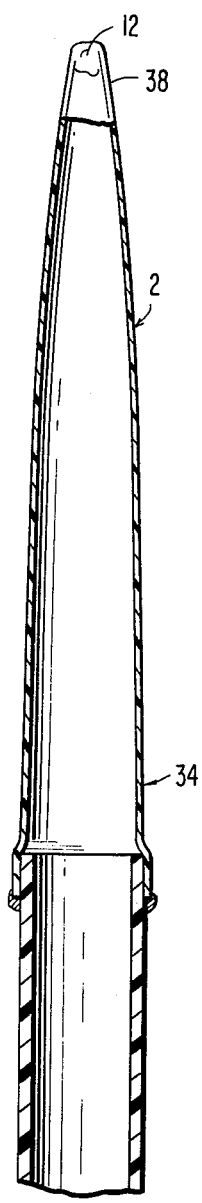
FIG. 7 is a fragmentary sectional view showing the flexible hose fulled everted.
Figure 8:
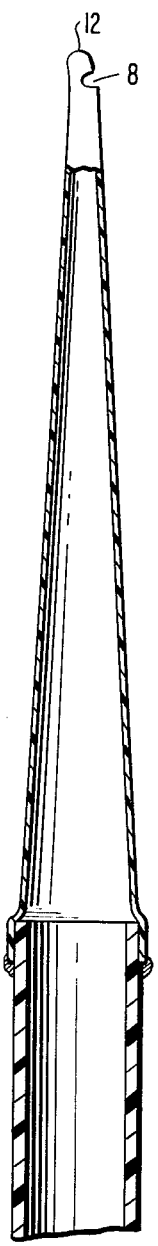
FIG. 8 is a fragmentary sectional view of the final stage in evagination of the catheter.

When the hose 2 has been fully everted, the distal end 38 of the catheter 34 will have entered the bladder (not shown), but the catheter will still be stoppered (see FIG. 7). Application of a small amount of additional pressure from the syringe 32 will then "pop" the stopper end 12 from the hose 2 (see FIG. 8) opening the port 8 so that urine may be withdrawn from the bladder for examination or drainage. Alternatively, the ported catheter may be used to medicate the bladder or serve as a sterile passage for insertion of a diagnostic instrument into the bladder. Upon completion of the required operation, the catheter is simply removed by pulling upon the proximal end 36. Since the new catheters can be made inexpensively, they can be handled as disposable items designed for one-time use. The new catheters can also be used for the introduction of x-ray opaque media used in the procedure of cystography.

The embodiments of the invention in which an exclusive property or privilege is claimed are defined as follows:

1. In an evagination catheter comprising a substantially rigid tube, a flexible hose shorter in length than said tube, the proximal end of said hose being in fluid-tight engagement with the distal end of said tube, said hose being inserted into said tube and structured to be exserted therefrom upon introduction of fluid pressure through the proximal end of said tube, and valve means on the distal end of said hose structured to remain closed when said hose is inserted in said tube and to open when said hose is completely exserted from the tube, the improvement wherein said valve means consists of a port cut through the side wall of said hose adjacent the distal end, the tip of the hose distal of said port being inverted forming a cup-shaped pendant on said hose which is inserted into the hose through said port forming a removable stopper for said port, said improvement being formed by providing a substantially rigid tube open at both ends and a flexible hose shorter in length and smaller in diameter than said tube, said hose having a closed end and an open end, cutting a port in the side of the hose adjacent said closed end having the tip of the hose's closed end pendant upon the hose, turning said tip inside out forming a cup-shaped pendant on the hose and inserting it into the hose through said port forming a stopper for said port, inserting the stoppered hose into said tube leaving a short section of the open end of said hose external of said tube, folding said short section of hose back over the outside of said tube and forming a fluid-tight connection between said folded back short section of hose and the adjoining outside of said tube.

* * * * *